(12) United States Patent
Diver et al.

(10) Patent No.: US 8,980,190 B2
(45) Date of Patent: Mar. 17, 2015

(54) PLASMA GENERATION AND USE OF PLASMA GENERATION APPARATUS

(75) Inventors: Declan Andrew Diver, Glasgow (GB); Hugh Potts, Glasgow (GB)

(73) Assignee: The University Court of The University of Glasgow

(*) Notice: Subject to any disclaimer, the term of this patent is extended or adjusted under 35 U.S.C. 154(b) by 0 days.

(21) Appl. No.: 13/504,867

(22) PCT Filed: Nov. 3, 2010

(86) PCT No.: PCT/GB2010/002031
§ 371 (c)(1),
(2), (4) Date: Apr. 27, 2012

(87) PCT Pub. No.: WO2011/055113
PCT Pub. Date: May 12, 2011

(65) Prior Publication Data
US 2012/0213664 A1    Aug. 23, 2012

(30) Foreign Application Priority Data
Nov. 3, 2009  (GB) .................................. 0919274.1

(51) Int. Cl.
*B01J 19/08*    (2006.01)
(52) U.S. Cl.
USPC ................................ 422/186.05; 422/186.04
(58) Field of Classification Search
USPC ....................................... 422/186.05, 186.04
See application file for complete search history.

(56) References Cited

U.S. PATENT DOCUMENTS 3,967,131 A    6/1976    Slipiec et al.
6,007,770 A    12/1999    Peiper et al.
(Continued)

FOREIGN PATENT DOCUMENTS

CN    101472384 A    7/2009
DE    202008008733 U1    12/2009
(Continued)

OTHER PUBLICATIONS

International Search Report and Written Opinion mailed Feb. 24, 2011 for International Patent Application No. PCT/GB2010/002031.
(Continued)

*Primary Examiner* — Kishor Mayekar
(74) *Attorney, Agent, or Firm* — David Bradin

(57) ABSTRACT

A plasma generating apparatus comprises a first, powered electrode and a second electrode structure located in front of the first electrode. An insulating layer is interposed between the first electrode and the second electrode structure. The second electrode structure has a plurality of second electrode portions defining gap portions therebetween. The width of the gap portions is w. The second electrode portions each have a forward surface and the gap portions each having a forward surface, the height difference between the forward surface of each second electrode portion and the forward surfaces of the adjacent gap portions being h, and wherein h is at most 1 mm and the ratio w/h is at least 1. Thus, the forward surfaces of the second electrode portions and the forward surfaces of the gap portions together provide a smooth topography. The plasma generated by the apparatus (in air or other oxygen-containing gas) forms ozone, which can be used to treat foodstuffs, for example. The smooth topography allows substantially all of the plasma to be generated inside a package whose wall is pressed towards the second electrode structure.

19 Claims, 7 Drawing Sheets

(56) References Cited

U.S. PATENT DOCUMENTS

| | | | |
|---|---|---|---|
| 6,200,539 B1 | 3/2001 | Sherman et al. | |
| 6,849,306 B2 | 2/2005 | Fukuda et al. | |
| 7,588,750 B2 * | 9/2009 | Ifland | 423/581 |
| 8,309,033 B2 * | 11/2012 | Finn et al. | 422/186.05 |
| 8,430,995 B2 * | 4/2013 | Murokh | 204/164 |
| 8,475,724 B2 * | 7/2013 | Kono et al. | 422/186.05 |
| 2003/0108460 A1 * | 6/2003 | Andreev et al. | 422/186.07 |
| 2004/0035532 A1 | 2/2004 | Jung | |
| 2004/0037756 A1 | 2/2004 | Houston et al. | |
| 2006/0022606 A1 * | 2/2006 | DeVries et al. | 315/169.4 |
| 2006/0042545 A1 | 3/2006 | Shibata et al. | |
| 2006/0162741 A1 | 7/2006 | Kurunczi | |

FOREIGN PATENT DOCUMENTS

| | | | |
|---|---|---|---|
| EP | 1507281 | | 2/2005 |
| JP | 2009-129817 | | 6/2009 |
| WO | WO 2006/039883 | | 4/2006 |
| WO | WO 2007/332321 | * | 3/2007 |
| WO | WO 2009/040130 | | 4/2009 |
| WO | WO 2009/098662 | | 8/2009 |

OTHER PUBLICATIONS

Search Report dated May 5, 2010 for corresponding Great Britain Application No. GB 0919574.1.

Schwabedissen et al., "PlasmaLabel-a new method to disinfect goods inside a closed package using dielectric barrier discharges" Contrib. Plasma Phys. 47 No. 7, 2007, pp. 551-558.

Bastien et al., "Accoustics and gas discharges: applications to loudspeakers" J. Phys. D: Appl. Phys. 20, 1987, pp. 1547-1557.

Bonova et al., "Cleaning of Aluminum Surface Using Diffuse Coplanar Surface Barrier Discharge", Chem. Listy 102, 2008, pp. 1452-1454.

* cited by examiner

US 8,980,190 B2

PLASMA GENERATION AND USE OF PLASMA GENERATION APPARATUS

RELATED APPLICATIONS

This application is a 35 U.S.C. §371 national phase application of PCT/GB2010/002031(WO 2011/055113), filed on Nov. 3, 2010, entitled "Plasma Generation and Use of Plasma Generation Apparatus", which application claims the benefit of GB patent application Ser. No. 0919274.1, filed Nov. 3, 2009, which is incorporated herein by reference in its entirety.

BACKGROUND OF THE INVENTION

1. Field of the Invention

The present invention relates to plasma generation apparatus and use of plasma generation apparatus. The invention has particular, but not exclusive, application to the sterilization of goods and/or surface decontamination.

2. Related Art

It is known that electrical discharges may be produced deliberately in order to provide useful effects. It is known, for example, to produce ozone ($O_3$) using a corona discharge in air at atmospheric pressure. For example, U.S. Pat. No. 3,967,131 discloses a corona discharge ozone generating unit in which a corona discharge is generated between concentric electrodes separated by an air gap and a cylindrical dielectric (glass) shield and connected to an ac voltage of about 12,000 volts. The electrodes are formed from stainless steel mesh.

A corona discharge is a form of plasma, i.e. a partially ionized gas, including a proportion of free electrons and ions, including excited neutral species.

The production of ozone is of interest in particular for sterilization and water-treatment applications, since ozone can render harmless micro organisms such as bacteria, and yet itself is unstable and degrades to oxygen in a relatively short time. Sterilization using ozone has many potential advantages over competing technologies such as heating, chemical disinfection, UV radiation and nuclear radiation.

U.S. Pat. No. 6,007,770 discloses an apparatus and method for sterilizing objects held in a closed vessel, such as in a sealed plastic bag. The apparatus has two parallel high voltage electrodes facing each other via two parallel insulators, there being a gap between the two parallel insulators. The closed vessel is placed in the gap between the parallel insulators. Operation of the apparatus causes oxygen in the closed vessel to be converted to ozone. The electrodes are operated at a voltage of 7-25 kV.

U.S. Pat. No. 6,007,770 discloses an embodiment in which there is an internal electric conductor in the closed vessel. This allows a lower applied voltage to be used. However, this document also explains that where the closed vessel is narrow, there may be no need for an internal electric conductor in the closed vessel.

It is considered that the operation of the device in U.S. Pat. No. 6,007,770 would generate ozone outside the closed vessel, resulting in a significant operator hazard. Furthermore, where no internal electric conductor is located in the closed vessel, the closed vessel must have a very small lateral extent (e.g. up to about 10 mm) in order to limit the applied voltage. Even so, a high voltage must be used, causing a very high electric field across the closed vessel, which will have the result of damaging sensitive items, including items containing electronics components. Furthermore, when the vessel includes conductive items (for example most foodstuffs), the arrangement of those conductive items will affect the amount of ozone produced, and can cause hotspots that damage the vessel.

US 2003/0108460 discloses a method and apparatus for producing a surface corona discharge. A base electrode and a mesh electrode are separated by a dielectric spacer. The mesh electrode is grounded. An ac voltage of 2.5-3.6 kV at 60 Hz is applied to the base electrode to produce a surface corona discharge for the production of ozone. The corona discharge is formed in the openings in the mesh electrode. US 2003/0108460 discloses the sterilization of objects in a plastic bag, such as tissues, organs, food products, etc. In this case, a lid of the plastic bag is formed with the ozone-producing apparatus, separated from the remainder of the volume of the plastic bag by a porous dielectric plate. Ozone produced by the ozone-producing apparatus disperses to the objects in the plastic bag through the porous dielectric plate. Thus, it is a requirement of US 2003/0108460 that there is no seal between the ozone-producing apparatus and the objects in the plastic bag, otherwise ozone cannot reach the objects in the plastic bag.

Schwabedissen et al 2007 [A. Schwabedissen, P Lacinski, X. Chen and J. Engemann, "PlasmaLabel—a new method to disinfect goods inside a closed package using dielectric barrier discharges" Contrib. Plasma Phys. 47 No. 7, 551-558 (2007)] disclose a ozone-based sterilization procedure. WO 2006/039883 provides a similar disclosure.

Schwabedissen et al disclose the generation of an atmospheric pressure plasma inside a sealed package by relying on a surface dielectric barrier discharge supported by a label on the inner surface of the package. The label includes a metallic electrode, here designated the inner electrode. An outer electrode arrangement is placed in contact with the outer surface of the package, and a high voltage ac signal is applied to the outer electrode arrangement. The outer electrode arrangement is capacitively coupled to the inner electrode, thereby driving a surface dielectric barrier discharge inside the sealed package and generating ozone.

The inner electrode used by Schwabedissen et al has a complex shape. This is in order to maximise the inner electrode edge length on the label, since the electric field strength is high at these edges. The metal of the inner electrode faces the interior of the package.

SUMMARY OF THE INVENTION

The present inventors have realised that the prior art disclosures identified above each suffer from disadvantages, for example relating to safety of operation, ease of implementation and/or ease of use. Furthermore, the present inventors consider that one, some or all of the disadvantages of the prior art can be addressed using the present invention.

Accordingly, in a first preferred aspect, the present invention provides a plasma generating apparatus comprising:
  a first electrode;
  a second electrode structure located in front of the first electrode;
  an insulating layer interposed between the first electrode and the second
  electrode structure,
wherein the second electrode structure has a plurality of second electrode portions defining gap portions therebetween, the width of the gap portions being w, the second electrode portions each having a forward surface and the gap portions each having a forward surface, the height difference between the forward surface of each second electrode portion and the forward surfaces of the adjacent gap portions being h, and wherein h is at most 1 mm and the ratio w/h is at least 1.

In a second preferred aspect, the present invention provides a use of a plasma generating apparatus, the plasma generating apparatus comprising:

a first electrode a second electrode structure located in front of the first electrode an insulating layer interposed between the first electrode and the second electrode structure wherein the second electrode structure has a plurality of second electrode portions defining gap portions therebetween, the width of the gap portions being w, the second electrode portions each having a forward surface and the gap portions each having a forward surface, the forward surfaces of the second electrode portions and the forward surfaces of the gap portions together forming a package treatment surface, the height difference between the forward surface of each second electrode portion and the forward surfaces of the adjacent gap portions being h, and wherein h is at most 1 mm and the ratio w/h is at least 1, the use comprising placing a package to be treated against the package treatment surface and operating the apparatus to generate plasma, the generated plasma being substantially wholly located in the package being treated.

In a third preferred aspect, the present invention provides a sterilizing arrangement of a plasma generating apparatus according to the first aspect and at least one package (and preferably a series of packages) to be treated.

Preferred and/or optional features will now be set out. These may be combined singly or in any combination with any aspect of the invention, unless the context demands otherwise.

Preferably, the forward surfaces of the second electrode portions and the forward surfaces of the gap portions together provide a smooth topography. This is preferred in order that plasma is generated substantially evenly across the forward surface of the device. This allows all of the plasma to be utilized, Furthermore, it allows the surface of the apparatus to be maintained (e.g. cleaned) more easily. This is of particular importance where the apparatus is for use in providing or maintaining a sterile or disinfecting atmosphere (such as in a chamber, e.g. for storage or manipulation of objects susceptible to degradation by bacteria, fungi, viruses and the like).

Preferably, the value for h is sufficiently small and/or the value for the ratio w/h is sufficiently large that, in use, the plasma is generated substantially wholly (or, in the most preferred case, only) in front of the forwardmost of the forward surfaces of the second electrode portions and the forward surfaces of the gap portions.

It is possible that the second electrode structure has a substantially planar configuration. However, this is not essential. The second electrode can have any configuration that makes it suitable to the task of generating plasma as required. For example, the second electrode can have a convex or a concave configuration, in at least one dimension or in two dimensions. Even a "saddle-shaped" (convex in one dimension, concave in an orthogonal dimension) is contemplated. Thus, the term "forward" is intended to specify a location that is, locally, further in front of (i.e. further away from) the first electrode than the second electrode. The forward direction can be considered to be along a line directed away from both the first electrode and the second electrode, the line being perpendicular to a tangent to the overall shape of the second electrode.

Preferably, h is at most 0.9 mm, at most 0.8 mm, at most 0.7 mm, at most 0.6 mm, at most 0.5 mm, at most 0.4 mm, at most 0.3 mm, at most 0.2 mm, or at most 0.1 mm. In particular, the inventors have found that h in the range 0-0.3 mm provides excellent performance.

Preferably, the ratio w/h is at least 1. More preferably, this ratio is at least 2, at least 4, at least 5, at least 6, at least 8, at least 10, at least 20, at least 30, at least 40, at least 50, or at least 100.

Preferably, w is from 0.1 to 2 times, more preferably 0.2 to 2 times (e.g. about 0.4, 0.6 or 0.8 times), the spacing distance between the first electrode and the second electrode. This allows the electric field from the first electrode to leak out through the gaps in a controlled manner, in order more controllably to form plasma at acceptable voltages. However, the preferred range for w depends to an extent on the shape of the second electrode. It is considered at present that the optimum value for w for a spiral (or approximate spiral) configuration for the second electrode is about 0.4, whereas for a hexagonal configuration second electrode, w may be 0.6 to 0.8 to achieve optimum performance. The distance between the first electrode and the second electrode structure may preferably be in the range 0.1-10 mm, more preferably in the range 0.1-5 mm or 0.1-2 mm, or in the range 1-10, 1-5 mm or 1-2 mm.

It is intended here that the measurement of h and the measurement of w/h is carried out substantially ignoring random surface roughness. The second electrode portions are preferably regularly arranged, this regular arrangement being non-random. For example, preferably the second electrode portions together form a substantially radial and/or substantially spiral pattern. Alternative arrangements are possible, e.g. a grid pattern or a honeycomb (e.g. hexagonal) pattern.

Preferably, the gap portions comprise dielectric material. In this way, the forward surfaces of the gap portions are dielectric material surfaces.

It is possible for each second electrode portion to include a conductive element with an overlying insulating layer, so that the forward surface of the second electrode portions is an insulating surface. This is preferred where it is wanted to cover the second electrode in use, for example to protect the second electrode from environmental degradation. A suitable overlying insulating layer can also be more readily cleanable than the second electrode itself. Thus, the term "second electrode portion" should not necessarily be interpreted as requiring a conductive portion alone—it is contemplated that the second electrode portion also includes the overlying insulating layer, if present.

In the case where there is an insulating layer overlying the conductive element, preferably this insulating layer extends into the gap portion adjacent the second electrode portion. In this way, it is possible for the forward surface of the second electrode portion and the forward surface of the gap portion to be continuous with each other, and formed of the same material. In one embodiment, this allows the forward surface of the apparatus to be smooth (e.g. flat) apart from random roughness (which is preferably minimized). Such an apparatus provides a readily cleanable surface. The insulating layer may be a material such as glass, mica, a plastic or ceramics.

In alternative embodiments, each second electrode portion may comprise a conductive element which is exposed at the forward surfaces of the second electrode portions. In this manner, the second electrode is typically visible to the user (and touchable by the user). However, typically the second electrode structure is connected to ground. In this way, the second electrode does not pose any electrical risk to the user. Furthermore, preferably the conductive elements of the second electrode portions are at least partially embedded in the surface of the device. For example, the forward surface of the gap portions may be located forwardly of the rearward surface of the adjacent second electrode portions. In this way, h can be reduced. It is possible in such embodiments for h to be substantially zero, where the forward surfaces of the conductive element are level with the forward surfaces of the gap portions.

The first electrode is typically connected or connectable to a signal generation source, for applying an ac voltage signal to the first electrode. The first electrode is typically located inside the apparatus, and is not exposed for contact with the user. For example, the first electrode may be held within an insulating casing. The exterior of the casing may be connected (or connectable) to ground.

The magnitude of the signal applied to the first electrode is preferably at least 0.5 kVrms, more preferably at least 1 kVrms. The magnitude of the signal applied to the first electrode is preferably at most 30 kVrms, more preferably at most 15 kVrms, or at most 8 kVrms. The frequency of the signal applied to the first electrode is preferably in the kHz range, but it is considered that the apparatus would operate satisfactorily (although less well than in the kHz range) if operated at 50-60 Hz. More preferably, the frequency of the signal applied to the first electrode is at least 1 kHz. Still more preferably, frequency of the signal applied to the first electrode is at least 5 kHz or at least 10 kHz. Preferably, frequency of the signal applied to the first electrode is at most 200 kHz, more preferably at most 100 kHz, still more preferably at most 50 kHz. These preferred limits of the ranges for magnitude and frequency of the signal applied to the first electrode are combinable in any combination.

It is preferred that the apparatus is operated in a pulsed mode, although continuous mode operation is possible. The main reason why pulsed mode is preferred is to control the thermal load on the package, particularly where the package is formed from a plastics material. Typically, duty cycles in the range 5-100% may be used. Preferably, duty cycles in the range 30-50% are used. Typical cycle times range from 0.05 s to 2 s. Preferably, cycle times in the range 0.2-0.4 seconds are used. For example, for a 50% duty cycle with a 0.2 s cycle time, the plasma would be cycled on for 0.1 s and off for 0.1 s repeatedly.

It is possible for the second electrode not to be connected to ground but instead to have a signal applied to it. In this case, it is preferred that the signal has a predetermined phase relationship with the signal applied to the first electrode. For example, the signal applied to the second electrode may be exactly out of phase with the signal applied to the first electrode. Preferably, the magnitude of the signal applied to the second electrode is smaller than (and most preferably significantly smaller than) the magnitude of the signal applied to the first electrode. This allows the further reduction of leaked electrical interference from the device (i.e. reduction in the leaked electrical field at distances away from the device).

Preferably, the insulating layer interposed between the first electrode and the second electrode structure completely fills the space between the first electrode and the second electrode structure. This is advantageous because otherwise, if there were gas-filled spaces between the first electrode and the second electrode structure, a plasma may be generated in such spaces, which would reduce the efficiency and longevity of the apparatus.

In one particularly preferred configuration, the apparatus is suitable for treating a package. In this case, the forward surfaces of the of the second electrode portions and the forward surfaces of the gap portions together preferably form a package treatment surface. In use, the package to be treated is placed against the package treatment surface. The apparatus is then operable to generate plasma. Preferably, the generated plasma is then substantially wholly located inside the package to be treated. The significant advantage of this is that the product of the plasma (e.g. ozone) can be formed only inside the package, so that the user is not exposed to significant quantities of the product of the plasma.

Preferably, the package treatment surface and the package conform with each other in use in order to limit the size of gaps between the package treatment surface and the package. The limitation (or even elimination) of such gaps reduces the volume, external of the package, within which plasma can form.

Preferably, in use, at least a part of the package is overlaid over the whole of the second electrode structure. In this way, an area size of the part of the package that is conformed with the package treatment surface can be larger than the second electrode structure. This assists in ensuring that the plasma is generated only inside the package and not outside the package.

The apparatus may further have urging means operable to press the package and the package treatment surface towards and against each other. For example, the urging means may be provided by a pressure differential. Such can be provided by suction means in fluid communication with the package treatment surface. Preferably, the package treatment surface includes channels for drawing air away from gaps between the package and the package treatment surface, said channels optionally being provided by the gap portions between the second electrode portions. The channels may be provided in a substantially radial and/or substantially spiral pattern at the package treatment surface.

The apparatus may further include at least one seal, provided in order to substantially seal with the package in use, optionally extending around the perimeter of the package treatment surface.

Preferably, the apparatus includes switching means, operable to energise the first electrode only when the urging means has caused the package and the package treatment surface to be pressed towards and against each other. For example, where the urging means are provided by suction, a predetermined value of drop in pressure in a suction line may be taken to indicate adequate pressing of the package and the package treatment surface towards and against each other. In this way, the switching means can act as a safety device, to avoid the apparatus generating plasma when a package is not pressed to the package treatment surface.

In an alternative embodiment, the package treatment surface may be flexible in order that it is capable of conforming to the package to be treated. Additionally, the package treatment surface may be resilient. For example, before the package treatment surface is conformed to the package, it may have a convex shape. This is of particular utility where the package is formed of rigid material, e.g. glass or rigid plastic.

Preferably, the package includes at least one object to be treated, selected from plant material, foodstuff, animal material, medical objects, ophthalmic objects and pharmaceutical or cosmetic products. Of particular interest here are perishable food products such as bakery products (such as fresh bread), fresh fruit, fresh vegetables, fresh meat, fresh fish, etc. However, it is possible for the package to include only a gas, such as air. In that case, it may be of interest to treat the air in the package as set out above, in order to use the treated air elsewhere, the package being used to contain and convey the treated air.

Typically, the package is substantially air tight during treatment with the apparatus. The package may include at least one seal for maintaining substantial airtight integrity until the package is opened by a user. The seal may be irreversibly broken by opening. Alternatively, the seal may be re-sealable after opening by the user. However, this is not essential in situations where the products of the plasma can be allowed to leak away from the package in safety.

In an alternative embodiment, it is possible for the package to be used as an enclosure to manipulate one or more objects. Such a object may be placed in the enclosure through a sealable opening. Before, during or after treatment of the enclosure using the apparatus, the object may be manipulated inside the enclosure, e.g. in order to open the object, or carry out some other process on the object. This manipulation may be assisted when the enclosure includes one or more flexible manipulation areas (typically two). For example, a flexible manipulation area may be provided by a portion of the enclosure in the form of a glove, allowing a user to insert a hand into the glove, thereby allowing the user to "insert" a hand into the internal space of the enclosure, whilst being separated from the internal space of the enclosure by the thickness of the glove, to carry out manipulation of the object. During this process, the overall enclosure, including the flexible manipulation area, preferably remains substantially sealed. In effect, the preferred format of this embodiment is a disposable glovebox. This embodiment is particularly preferred where the object for manipulation includes one or more biohazardous materials, e.g. for manipulation in the field, or simply where a disposable or collapsible enclosure can be justified (e.g. where its use would be infrequent) and where the cost and/or and space for a conventional glovebox cannot be justified.

The package may include a packaging atmosphere at or near atmospheric pressure. The packaging atmosphere preferably includes oxygen (e.g. at least 1% oxygen and preferably at least 5% or at least 10% oxygen). For example, the packaging material may be air. Alternative atmosphere are also contemplated. For example, the treatment of the container may be in order to remove a reactive gas or contaminant from the atmosphere inside the package. In one embodiment, a toxic volatile organic compound may be given off by materials (e.g. glues) used in the manufacture of an object. A plasma can oxidise these toxic volatile organic compounds, rendering them relatively safe. In another embodiment, active species generated by a plasma in pure nitrogen may be useful for destroying specific unwanted compounds.

Certain gas mixtures are used in modified atmosphere food packaging (MAP), to which processes preferred embodiments of the present invention have particular utility. Thus, for example, the atmosphere may contain an enhanced level of a gas such as oxygen or carbon dioxide as is commonly used in modified atmosphere food packaging (MAP).

It is preferred that the plasma is an ozone-generating plasma. This is of particular interest for sterilization applications, but the present invention is not necessarily limited to sterilization applications. Typically, ozone is generated by the plasma due to the formation of oxygen radicals and ions from oxygen molecules, with reactions between these three species leading to the formation of ozone.

Ozone is an excellent sterilizing/disinfecting agent, and is considered to be especially useful for treating packaged consumer items, such as packaged food and packaged medical products. Ozone attacks and can render substantially harmless bacteria, fungi, viruses, spores, etc. At atmospheric pressure and ambient temperature, ozone has a usefully short half-life. After forming ozone in the package using the plasma, the amount of ozone decreases with time so that when (some time after the treatment) a consumer comes to open the package, the package contains little or no remaining ozone.

The package may be rigid, but is most preferably flexible, at least in the region intended to be urged against the generation surface of the apparatus. For example, the package may include a flexible polymeric layer. Known packaging plastics are particularly suitable, such as polypropylene (PP), biaxially-oriented polypropylene (BOPP), polyethylene (PE), polyethylene terephthalate (PET), combinations of these materials, etc. In the case of a rigid package (e.g. rigid plastic such as PET or in the case of glass packages) it is possible for the apparatus to conform to the outer shape of the rigid package.

It is preferred that the packaging itself is substantially without a conductive layer, such as a metallic layer. This does not exclude the possibility that the packaging includes discrete metallic components, such as fasteners (e.g. staples, wire fasteners, etc.) comprising metal. However, it is particularly preferred that the packaging does not include a conductive layer, such as a patterned conductive layer, for promoting the generation of plasma in the packaging. One reason for this is that the inclusion of such a layer requires modification of the packaging and/or of the packaging process. In contrast, use of the preferred embodiments of the present invention allows sterilization of pre-sealed packages without the requirement to add a further component into the packaging. This means, for example, that the package can be manufactured and sealed at one site, and transferred to the apparatus for later sterilization. A further disadvantage of the inclusion of a conductive layer in the packaging may interfere with the quality of the packaged product. For example, a metallic label in contact with packaged food may cause a change of taste, discolouration, etc. of the food.

In some embodiments, it is preferred to provide a plasma generating apparatus with a relatively large total "footprint" area for the first electrode and second electrode. This allows the generation of plasma over a correspondingly large area. The required electrode area can be provided by using suitably large, single first and second electrodes.

However, the inventors have realised that their system is scalable in size using a modular arrangement.

Accordingly, in a further aspect of the invention, there is provided a plasma generation system comprising a plurality of modules, each module providing at least a modular second electrode, the respective modular second electrodes being capable of being assembled into a plasma generating apparatus according to the first aspect in which the second electrode is provided by the assembly of modular second electrodes.

In the plasma generation system, it is possible for the first electrode to be provided as a single (i.e. non-modular) unit, cooperating with the modular second electrodes. However, it is preferred that the system comprises modular first electrodes arranged with respect to the corresponding modular second electrodes to allow assembly of the plasma generating apparatus.

Preferably, the modular second and/or modular first electrodes tessellate to form the required array of electrodes. The tessellation preferably provides a relatively uniform plasma distribution across the plasma generation surface.

Further optional features of the invention are discussed below.

BRIEF DESECRIPTION OF THE DRAWINGS

Preferred embodiments of the present invention are described below with reference to the accompanying drawings, in which.

DETAILED DESCRIPTION OF THE PREFERRED EMBODIMENTS, FURTHER OPTIONAL FEATURES OF THE INVENTION

Figure 1:
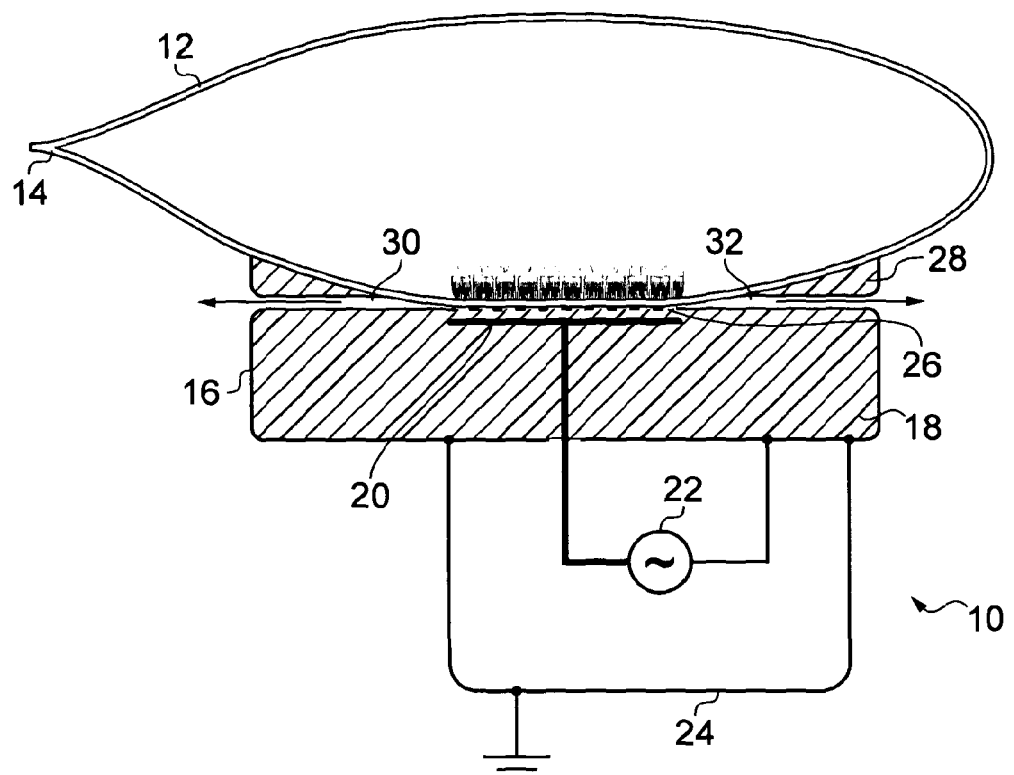
FIG. 1 shows a schematic cross sectional view of an apparatus in use according to one embodiment of the present invention.

FIG. 1 shows a schematic cross sectional view of a sterilizing arrangement according to a preferred embodiment of the invention. The sterilizing arrangement includes a plasma generating apparatus 10 and a package 12 to be treated, including at least one object (not shown, but typically a foodstuff such as fresh fruit/vegetables or a medical product such as a wound dressing) contained in the package 12.

The package in this embodiment comprises a flexible bag formed of plastics material, such as PE. A seal 14 is formed in a known manner at a previously open region of the package.

The plasma generating apparatus 10 includes a housing 16 formed of metal and electrically connected, in use, to ground. Housing 16 encloses an insulator 18 embedded in which is a first, powered, electrode 20. First electrode 20 is electrically connected to a signal generation source, high voltage power supply 22. High voltage power supply 22 is fully contained within earthed metallic shell 24.

The apparatus has a package treatment surface which is substantially coterminous with the footprint of second electrode 26. Second electrode 26 is metallic and is exposed at the treatment surface. In other embodiments, the second electrode may be covered with (or embedded in) a thin layer of insulating material. The second electrode 26 overlies and is in register with the first electrode 20. The first and second electrodes may have substantially the same overall footprint. The first and second electrodes are separated by a thin layer of insulating material 18.

Seal means, in the form of gas flow baffles 28, are provided around the generation surface. The seal means provide an inclined, continuous surface, for meeting and sealing with a corresponding part of the package. This allows the package to be supported on the apparatus at the beginning of the sterilization process, and allows the maintenance of a seal between the package and the seal means as the package is urged towards the package treatment surface, Between the gas flow baffles 28 and the housing 16 are provided gas flow passages 30, 32, connected to a vacuum pump (not shown). By operation of the pump, when the package is supported by the seal means, the air in the space between the package and the generation surface may be withdrawn. The pressure differential forces the package towards the generation surface, and ultimately presses the package against the second electrode. As the seal is completed (or at least improved), the reduced pressure in the vacuum line can be used to switch on the power to energise the first electrode.

The structure of the second electrode is carefully designed in order to avoid the creation of bubbles of trapped air between the package and the second electrode. For example, a suitable electrode structure may have an array of spiral branched arms, connected at a central node and at their extremities to earth. Between the arms are formed channels which allow air to be extracted from between the generation surface and the package without the formation of regions in which air may be trapped. Thus, on operation of the vacuum pump, the package is pressed evenly against the package treatment surface. In this embodiment, h and w describe the shape of the channels, which coincide with the gaps between the second electrode portions. The skilled person can easily measure these dimensions, and can distinguish them from random surface roughness in view of the regularity of placement of the second electrode portions and the gaps between them, For example, a surface profile measurement may be taken in order to measure these dimensions.

Figure 2:
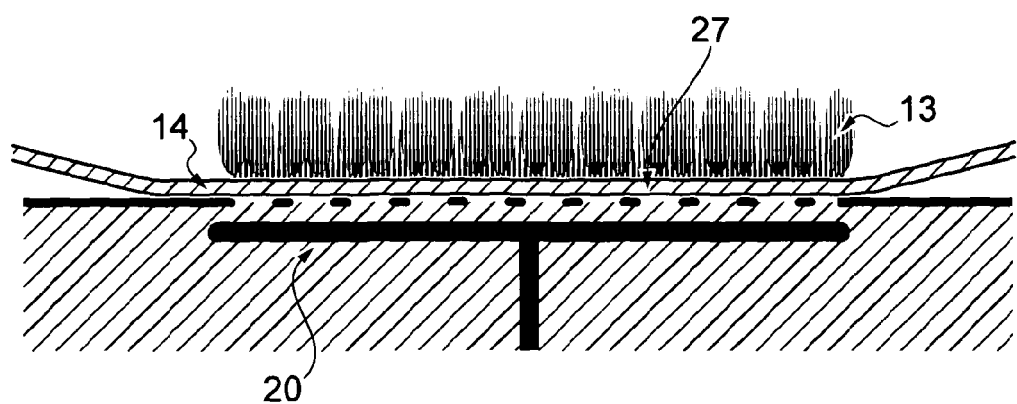
FIG. 2 shows an enlarged view of part of FIG. 1.

As shown more clearly in FIG. 2, operation of the first electrode 20 allows the generated electric field to "leak" out through the structured shape of the second electrode 26 (see gaps 27) and into the space above the second electrode. A plasma 13 forms in the regions of high electric field where there is gas (e.g. air) present. When the package bag is pressed firmly against the generation surface the layer of the package material forms an additional insulating layer at the generation surface, over the upper surface of the second electrode. However, this does not significantly affect the geometry of the electric field in practical terms. The plasma then forms above the layer of the package material, and hence inside the package.

In general, the gap between the arms of the second electrode is about 0.2-2 times the insulator gap between the two electrodes, and most preferably about 0.4 times.

As shown more clearly in FIG. 2 (an enlarged view of part of FIG. 1), the plasma is struck entirely within the package. The package is pressed to the package treatment surface so that the area size of the package pressed to the package treatment surface (or, more generally, pressed to the apparatus) is greater than the area size of the second electrode and hence greater than the area size of the plasma. This avoids the plasma being struck partially inside and partially outside the package (which can otherwise cause problems for the operator of the device). Ozone is therefore generated from the oxygen gas contained in the package.

It is to be noted that the present embodiment provides several important technical advantages. Firstly, in some prior art systems (e.g. Schwabedissen et at 2007), at least one powered electrode is provided exposed at the surface of the apparatus. This is very hazardous. In contrast, in the preferred embodiments of the present invention, there is no exposed component to which a high voltage is applied. This allows the present embodiments to be operated in high moisture conditions, high humidity conditions, or even underwater. The design of the second electrode of the preferred embodiments means that the electric field that leaks out decreases very rapidly with distance from the apparatus. This means in turn that any electrical interference provided by operation of the apparatus will be very low. The large size of the electrodes on the Schwabedissen system result in large radiated fields, posing serious regulatory problems, and making in-situ medical use difficult or unrealistic.

It is further to be noted that it is particularly advantageous that there is no metallic label to be provided in the package. One key advantage is that no special or modified packaging is required. Therefore the preferred embodiments of the invention can be used without requiring modification of existing packaging lines or packaging materials. This has a benefit also in efficiency and cost. Stock which has already been manufactured and packaged (e.g. old, pre-packaged medical stock) can be sterilized or re-sterilized before use. Furthermore, the absence of a metallic label avoids problems of metals in contact with food (reaction, taste, etc.). In the prior art apparatus, the problems associated with metal in contact with the packaged contents may indeed be more serious when the plasma is present, promoting adverse reactions inside the package.

As seen in FIG. 2, the forward surfaces of the conductive elements of the second electrode structure are shown as level with the forward surfaces of the adjacent gap portions. Therefore h is zero in this specific embodiment. However, it is possible for h to be non-zero, e.g. for the provision of shallow air drainage channels as discussed above. Such a situation (h being non-zero) arises for example if the second electrode structure is deposited on to the layer of insulating material covering the first electrode.

Figure 3:
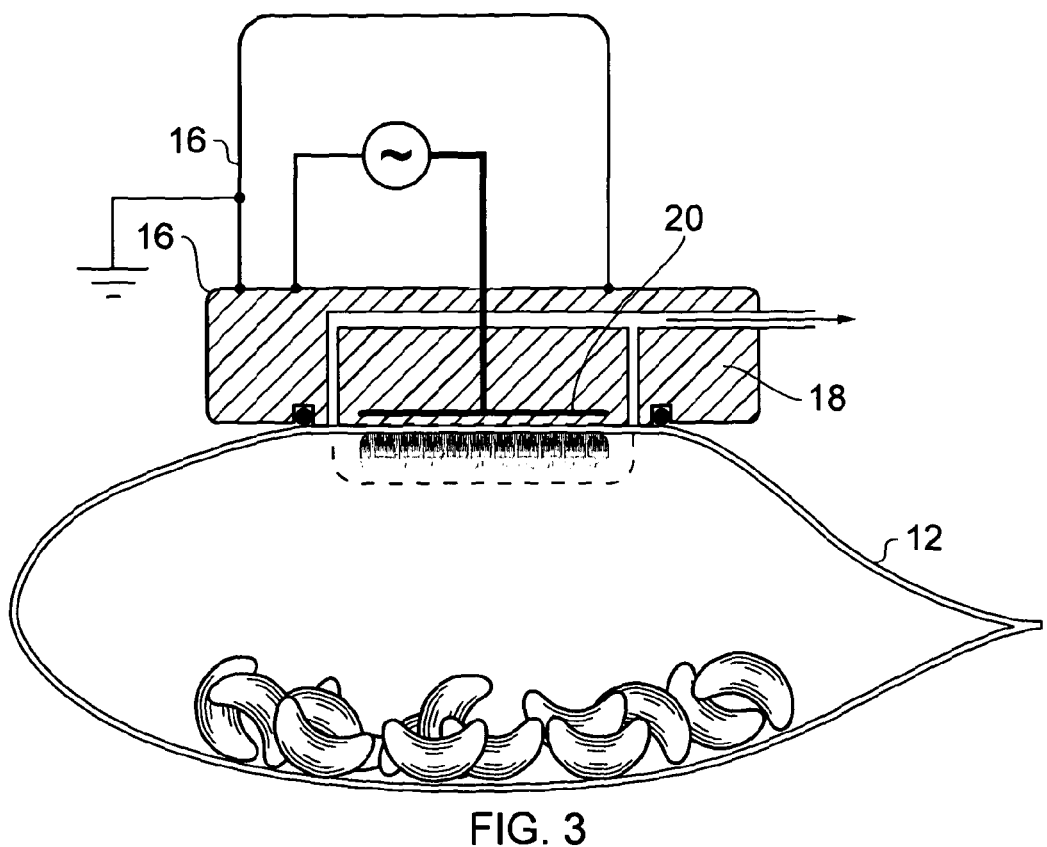
FIG. 3 shows a schematic cross sectional view of an apparatus in use according to another, more preferred, embodiment of the present invention.

FIG. 3 shows a modification of the embodiment of FIG. 1. Similar features as shown in FIG. 1 are given the same reference numbers as in FIG. 1 and are not described here again. In FIG. 3, the apparatus is inverted, in order that the material to be sterilized (in the package) is more easily kept away from the region of the package subjected to plasma treatment. The structure of the apparatus means that the strong electric field only penetrates a short distance into the package. The extent of penetration of the strong electric field is shown by the dashed line in FIG. 3. As with reference to FIG. 1, the plasma is formed substantially entirely within the package 12.

Figure 4:
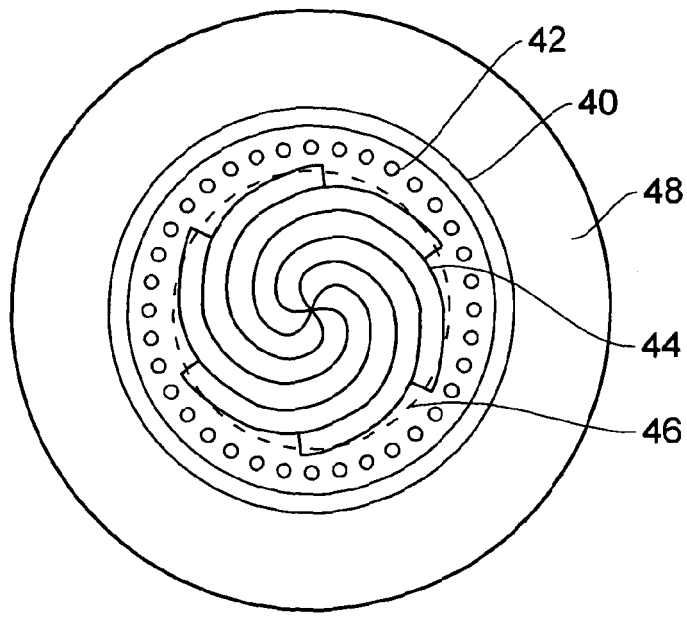
FIG. 4 shows a schematic plan view of a package treatment surface of the apparatus of FIG. 3.

The seal means used in FIG. 1 is different to that used in FIG. 3. In FIG. 3, an O-ring is located in a channel surrounding the second electrode structure. The sealing arrangement is shown more clearly in FIG. 4. O-ring 40 is located so as to project slightly from the package treatment surface (also called the generating surface). Vacuum ducts 42 are located to surround the second electrode structure 44, which overlies the first electrode (shown in phantom as 46 in FIG. 4). Earthed shield 48 is electrically connected to the second electrode structure, in order the that second electrode structure is also earthed, to ensure safe operation.

Figure 5:
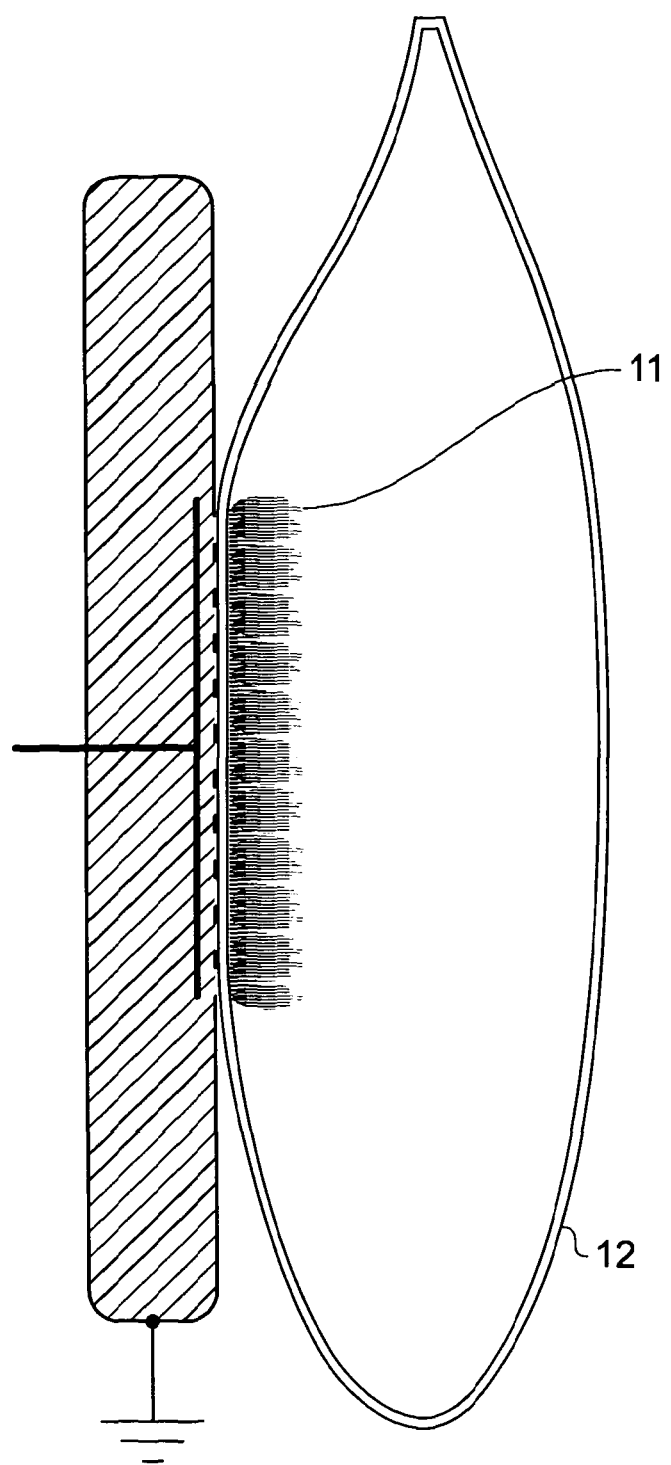
FIG. 5 shows a partial schematic cross sectional view of one implementation of the present invention.
Figure 6:
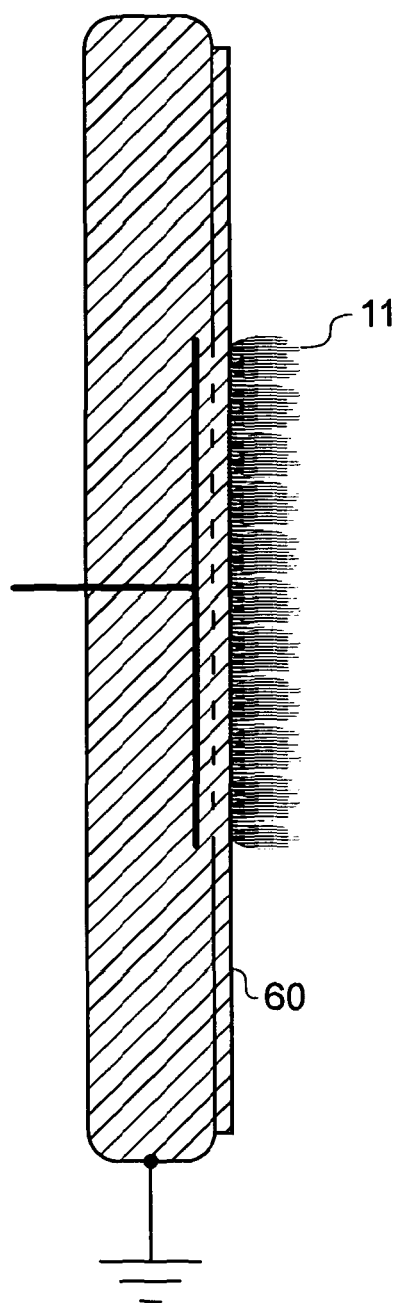
FIG. 6 shows a partial schematic cross sectional view of another implementation of the present invention.

FIG. 5 shows a partial schematic cross sectional view of one implementation of the present invention. In this implementation, the apparatus is used to treat a package 12. The conductive elements of the second electrode are exposed at the package treatment surface. However, when the package is urged towards the package treatment surface, the wall of the package itself covers the conductive elements of the second electrode, preferably leaving no significant gaps between the package treatment surface and the package. The effect of this is that when the first electrode is energised, the plasma 11 is formed only inside the package 12. In this way, ozone can be produced so that it is produced only inside a sealed bag package. This has particular utility for treatment of food, medical dressings, and medical instrument sterilization. It may also be used, for example, for the removal of gaseous contaminants from a sealed bag FIG. 6 shows a partial schematic cross sectional view of another implementation of the present invention. In FIG. 6, the apparatus can be used without a package, e.g. for surface disinfection. The conductive elements of the second electrode structure are located behind a thin layer 60 of insulating material, e.g. plastics (e.g. Teflon), ceramics, glass etc. This allows the plasma generating surface of the apparatus to be smooth, homogeneous and uniform, allowing easy cleaning for example, and allowing the second electrode to be completely hidden from view. Such an apparatus may be built into the walls of a biological safety cabinets, refrigerator (e.g. domestic refrigerator), microwave oven, dishwasher, rubbish (garbage) bins, etc., allowing sterilisation and odour control. Such an apparatus may also be built into the lid of a cosmetics box, for example.

Figure 7:
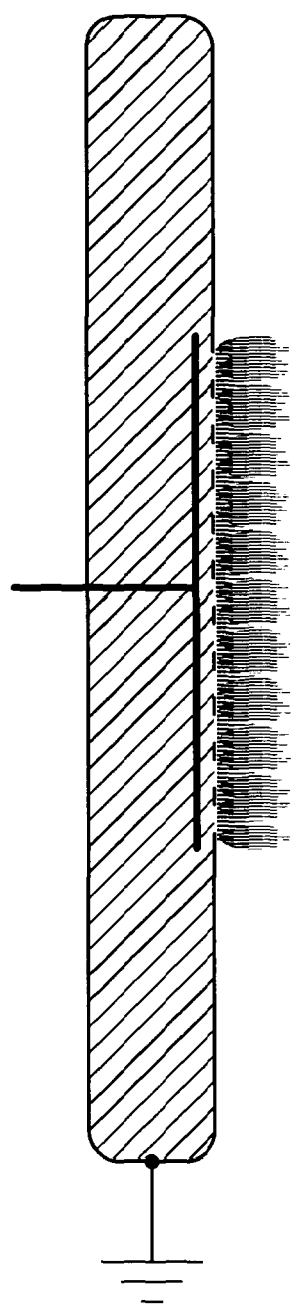
FIG. 7 shows a partial schematic cross sectional view of a further implementation of the present invention.

FIG. 7 shows a modification of FIG. 6, in which the insulating layer 60 is not present. It is intended that this apparatus has similar applications to the apparatus of FIG. 6.

Figure 8:
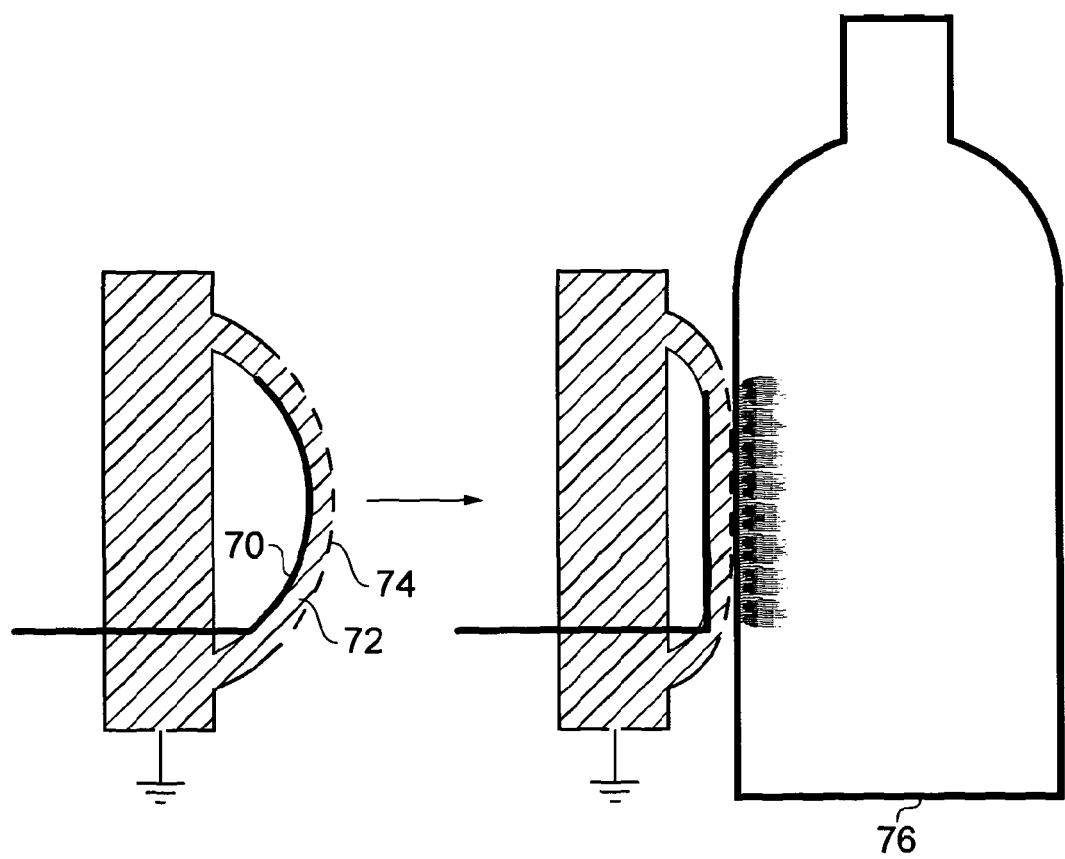
FIG. 8 illustrates a schematic view of another embodiment of the present invention.

FIG. 8 illustrates a schematic view of another embodiment of the present invention. In this embodiment, as shown in the left hand view of FIG. 8, the apparatus has a conformable package treatment surface. The first electrode 70 is located on one side of a resilient flexible insulating layer 72 (e.g. formed of insulating silicone polymer) and the second electrode structure 74 is located in the forward side of the resilient flexible insulating layer 72. The first and second electrodes can be formed of conductive silicone polymer, for example. Before use, the configuration of the resilient flexible insulating layer 72 (and thus of the electrodes) is convex. However, when pressed against a package (e.g. glass or plastic bottle 76), the package treatment surface conforms to the shape of the package. The aim here is to ensure that all of the second electrode structure is pressed to the wall of the package, in order that the plasma generated due to subsequent energisation of the first electrode is formed wholly within the package, thereby to form ozone only within the package. This apparatus does not required a vacuum pump, so can be smaller and manufactured more cheaply than the apparatus of FIG. 1. As will be understood, it is of particular interest for treating rigid packages. It should be noted here that FIG. 8 is schematic. In particular, the right hand view in FIG. 8 shows that, at the upper and lower extremities, the second electrode is not in close contact with the wall of the bottle. However, for practical implementations of the present invention, it is preferred that all of the second electrode is pressed in close contact with the wall of the bottle. This is to avoid the generation of plasma outside the bottle.

It is of interest here to consider the advantages of the present systems over known systems, For example, using the system of U.S. Pat. No. 6,007,770, ozone is produced both inside and outside the package, resulting in a significant operator hazard, and the requirement that to avoid operator hazard, the apparatus must be operated within a sealed enclosure. However, using the preferred embodiments of the present invention, ozone is produced only within the package where present, with automatic detection of safe operating conditions, e.g. based on the pressure in the vacuum line.

Furthermore, in U.S. Pat. No. 6,007,770, it is possible only to treat very thin packages (e.g. of total width only up to about 10 mm) unless a complex electrode structure is placed in the bag (see, for example, FIG. 3 of that document). Even then, very high voltages are required. With the preferred embodiments of the present invention, arbitrary packages can be treated provided that a small area of one side of the package is accessible.

In U.S. Pat. No. 6,007,770, the entire contents of the bag are exposed to a very high electric field, precluding the sterilising of many delicate items, especially those containing electronics. The exact arrangement of conductive items within the container would typically also have a significant effect on the amount of ozone produced, and could also cause hotspots that damage the bag. In the preferred embodiments of the present invention, the electric field region is confined to a small volume, close to the second electrode, so the package contents does not affect the amount of ozone produced, and also the package contents are not exposed to any significant electric field.

With respect to US 2003/0108460, it is considered that most of the plasma produced by the apparatus of that document would be produced within the spaces between the wire of the mesh electrode. This is because the most intense electric field region (where the plasma forms) in US 2003/0108460 occurs in this region. This would make it impossible to treat a package in such a way that the plasma is formed wholly inside the package, unless the whole plasma generation apparatus is located inside the package.

In a still further embodiment (not illustrated), the apparatus may be formed with a configuration to allow it to be inserted into a package or container. For example, the apparatus may be configured so that the second electrode structure is located on an insertion structure, the insertion structure being shaped and dimensioned to allow it to be inserted into the package or container. The first electrode is arranged in register with the second electrode structure. Of particular interest here is the treatment of packages or containers with relatively narrow openings in comparison to their overall size, such as bottles. Insertion of the insertion structure into such openings and operation of the apparatus to generate plasma allows treatment of the interior of the package or container, including the contents of the package or container. The apparatus may be adapted to seal with the opening of the package or container, for similar reasons as outlined above for sealing of a package to the apparatus. The provision of a smooth and uniform package treatment surface allows easy cleaning of the apparatus.

Suitable packaging structures to be treated with the preferred embodiments may also include tray packs. Such packs are typically encountered in industrial production line deployment, especially in the food industry.

It is preferred that the apparatus is operated in a pulsed mode, although continuous mode operation is possible. The main reason why pulsed mode is preferred is to control the thermal load on the package, particularly where the package is formed from a plastics material. In the preferred embodiments, duty cycles in the range 30-50% are used, with cycle times in the range 0.2-0.4 seconds. For example, for a 50% duty cycle with a 0.2 s cycle time, the plasma would be cycled on for 0.1 s and off for 0.1 s repeatedly.

With respect to the prototype unit (substantially according to FIG. 1), some performance data will now be set out. It is noted here that the prototype is not necessarily optimised.

Ozone concentrations: it is possible to produce up to 700 ppm ozone in air in a sealed bag. The inventors consider that significantly greater ozone concentrations can be achieved using their prototype apparatus, but they are limited by the performance of their diagnostics. It is considered possible to get very much higher concentration if the gas in the bag is pure oxygen Ozone production rate: it is possible to produce up to 72 mg ozone per second per square meter of generating area. These figures were obtained to the prototype system at 100% duty cycle though 35 micron polypropylene film with the plasma generated in air. Therefore, for example, to obtain an ozone concentration of 100 ppm in a 1 litre container with a 10 cm×10 cm electrode takes around 0.25 s. The ozone production rate can be substantially enhanced with higher oxygen concentration (e.g. using pure oxygen). In practice, a pulsed system is normally used (normally about 50% duty cycle, 0.2-1 s cycle time).

Power consumption: For the above ozone generation rate, power consumption of the prototype is 33 kW per square meter. Thus, for a 10 cm×10 cm electrode, power consumption is 330 W.

Figure 9:
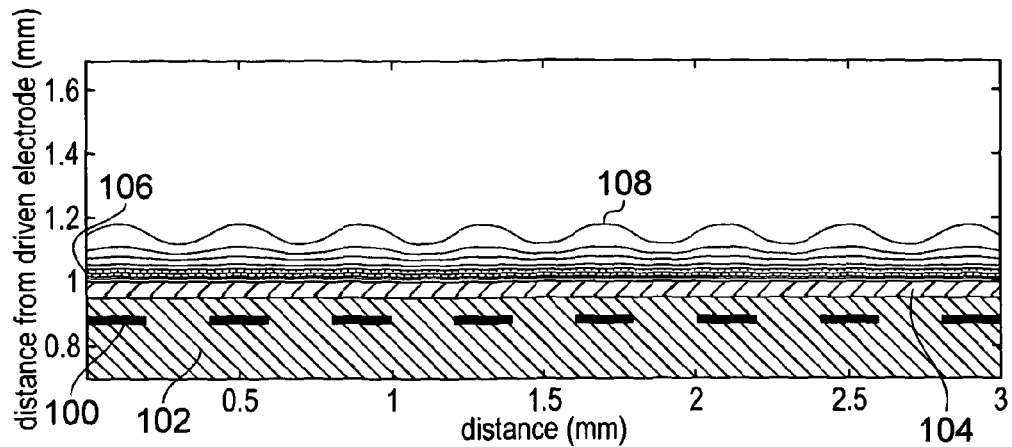
FIGS. 9-11 show schematic cross sectional views of part of various devices in use, producing plasma, and illustrating the penetration of the electric field and associated plasma into a plastic bag, the performance of each device varying with spacing in the second electrode member.
Figure 10:
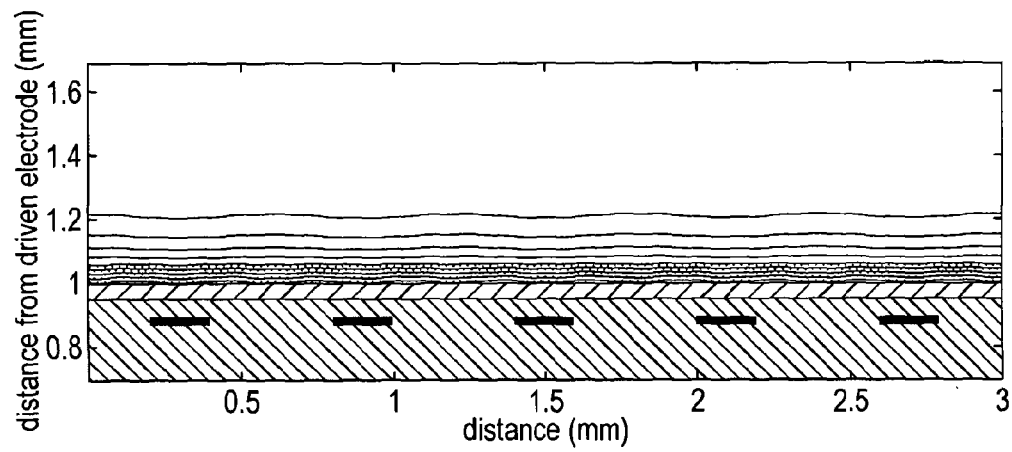
Figure 11:
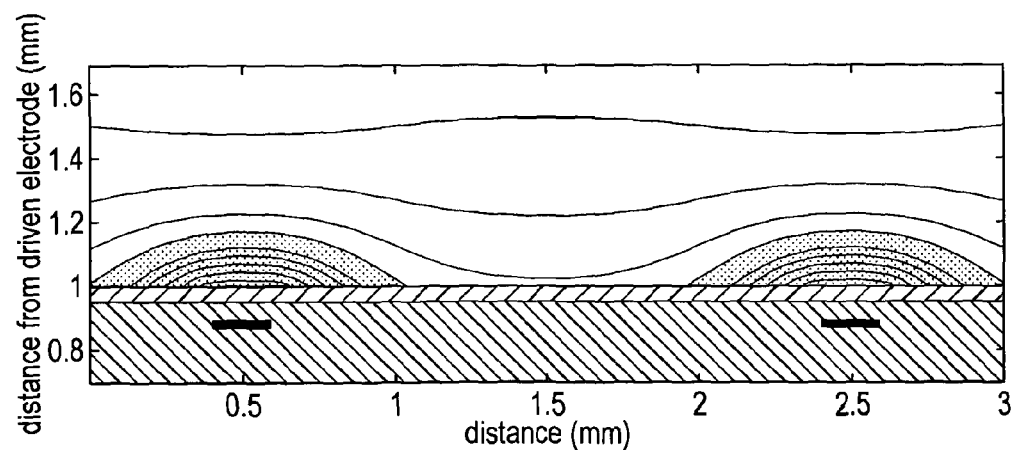

FIGS. 9-11 illustrate the effect of spacings in the second electrode on the electric field penetration into a plastic bag and thus the formation of plasma in the space inside the plastic bag.

In each of FIGS. 9-11 (but numbered only in FIG. 9), the second electrode 100 is embedded in a dielectric layer 102. A plastic bag 104 is located in close contact with the surface of the dielectric layer 102. A driving voltage is applied to the first electrode (not shown), the value of the driving voltage being 10 kV rms in FIG. 9, 3 kV rms in FIGS. 10 and 0.7 kV in FIG. 11. The second electrode is grounded. As a result, some electric field leaks through the second electrode. FIGS. 9-11 show contours of electric field strength 108 and the resultant plasma 106. As will be understood based on the description of the preferred embodiments above, it is desirable to form a uniform plasma inside the plastic bag, without the plasma or the electric field penetrating too far into the bag.

In FIG. 9, the spacing between the second electrode portions is 0.2 mm. This is shown to be too small. A very large driving voltage required (this is expensive and less safe). However, a relatively uniform plasma is produced. The electric field reduces rapidly away from the device.

In FIG. 10, the spacing between the second electrode portions is 0.4 mm. This appears to be the optimum spacing for this device. There is produced a thicker layer of uniform plasma, at much lower driving voltage than in FIG. 9. The electric field is strongly localised close to the second electrode structure and does not penetrate far into the interior of the bag.

In FIG. 11, the spacing between the second electrode portions is 1.8 mm. This is shown to be too large for this device. There is formed only discontinuous plasma only covering a small area of the second electrode structure. The electric field extends a considerable distance from the device surface, risking damage to the contents of the bag and generating electrical interference. It is to be noted, however, that only a small driving voltage is required.

In some embodiments, it is necessary to provide the plasma generating apparatus with a relatively large total "footprint" area for the first electrode and second electrode. This allows the generation of plasma over a correspondingly large area. The required electrode area can be provided by using suitably large, single first and second electrodes. However, it is more preferred to provide a required size for the apparatus by scaling up using a modular arrangement. Therefore a suitable plasma generation system comprises a plurality of modules, each module providing a modular first electrode and a modular second electrode. These modules can be assembled to allow the modular electrodes to tessellate to provide the required electrode structure with a suitable footprint for the application in hand. The tessellation preferably provides a relatively uniform plasma distribution across the plasma generation surface.

Furthermore, it is possible for the cross sectional shape of the second electrode to be adjusted to approach optimisation of performance of the apparatus. For example, the cross sectional shape of the second electrode may be elliptical.

The first electrode may be structured in a manner to approach optimisation of the performance of the apparatus. In particular, the first electrode need not be a completely planar structure. The first electrode may include protrusions (preferably smooth protrusions). These protrusions may be provided in register with corresponding shape features of the second electrode, e.g. with gaps in the second electrode. The protrusions may be provided in the form of one or more ripples. The protrusions preferably enhances the production of the plasma-producing electric fields at the apparatus surface. It is preferred that the first electrode is a continuous electrode, without gaps formed in it.

The present invention is not considered to be limited to application in the field of foodstuffs. Further applications of the technology are found in the fields of electronics, glass or other surface cleaning, automotive applications and deployment in temporary toilets and pit latrines to control odour and disease spread by exposure of human waste to airborne vectors.

The preferred embodiments of the invention have been described by way of example. Modifications of these embodiments, further embodiments and modifications thereof will be apparent to the skilled person on reading this disclosure, and as such are within the scope of the present invention.

The invention claimed is:

1. A plasma generating apparatus comprising:
a first electrode;
a second electrode structure located in front of the first electrode;
an insulating layer interposed between the first electrode and the second electrode structure,
wherein the insulating layer interposed between the first electrode and the second electrode structure completely fills the space between the first electrode and the second electrode structure,
wherein the second electrode structure has a plurality of second electrode portions defining gap portions therebetween, the width of the gap portions being w, the second electrode portions each having a forward surface and the gap portions each having a forward surface, the height difference between the forward surface of each second electrode portion and the forward surfaces of the adjacent gap portions being h, and
wherein h is at most 0.1 mm and the ratio w/h is at least 10, and wherein the second electrode structure is covered with a second insulating layer.

2. The apparatus according to claim 1 wherein w is from 0.2 to 2 times the spacing distance between the first electrode and the second electrode.

3. The apparatus according to claim 1 wherein the second electrode portions together form a substantially radial and/or substantially spiral pattern.

4. The apparatus according to claim 1 wherein the insulating layer covering the second electrode structure extends into the gap portion adjacent the second electrode portion, so that the forward surface of the second electrode portion and the forward surface of the gap portion are continuous with each other.

5. The apparatus according to claim 1 wherein each second electrode portion comprises a conductive element which is exposed at the forward surfaces of the second electrode portions.

6. The apparatus according to claim 1 wherein the second electrode structure is connected to ground.

7. The apparatus according to claim 1 wherein the first electrode is connected or connectable to a signal generation source, for applying an ac voltage signal to the first electrode.

8. The apparatus according to claim 7 wherein the first electrode is held within an insulating casing.

9. The apparatus according to claim 1 suitable for treating a package, the forward surfaces of the second electrode portions and the forward surfaces of the gap portions together forming a package treatment surface, wherein when the package to be treated is placed against the package treatment surface, the apparatus is operable to generate plasma, the plasma being substantially wholly located inside the package to be treated.

10. The apparatus according to claim 9, wherein the package treatment surface and the package conform with each other in use in order to limit the size of gaps between the package treatment surface and the package.

11. The apparatus according to claim 10, wherein in use at least a part of the package is overlaid over the whole of the second electrode structure, so that an area size of the part of the package that is conformed with the package treatment surface is larger than the second electrode structure.

12. The apparatus according to claim 10, further having urging means operable to press the package and the package treatment surface towards and against each other.

13. The apparatus according to claim 12 wherein the urging means is provided by suction means in fluid communication with the package treatment surface.

14. The apparatus according to claim 13 wherein the package treatment surface includes channels for drawing air away from gaps between the package and the package treatment surface, said channels optionally being provided by the gap portions between the second electrode portions.

15. The apparatus according to claim 14 wherein the channels are provided in a substantially radial and/or substantially spiral pattern at the package treatment surface.

16. The apparatus according to claim 13, further including at least one seal, provided in order to substantially seal with the package in use, optionally extending around the perimeter of the package treatment surface.

17. The apparatus according to claim 10 wherein the package treatment surface is flexible in order that it is capable of conforming to the package to be treated.

18. The apparatus according to claim 17 wherein the package treatment surface is resilient.

19. The apparatus according to claim 17 wherein the package treatment surface is convex, at least before it is conformed with the package.

* * * * *